United States Patent [19]

Nappi et al.

[11] Patent Number: 5,697,285
[45] Date of Patent: Dec. 16, 1997

[54] ACTUATORS FOR SIMULATING MUSCLE ACTIVITY IN ROBOTICS

[76] Inventors: Bruce Nappi, 15 Northgate Park, Newton, Mass. 02165; Donald Francis O'Brien, 221A Ash St., Waltham, Mass. 02154

[21] Appl. No.: 576,643

[22] Filed: Dec. 21, 1995

[51] Int. Cl.⁶ .............................. F15B 11/00; F15B 19/00
[52] U.S. Cl. ........................... 91/519; 91/530; 92/48; 92/34
[58] Field of Search ...................... 92/48, 92, 62, 92/63, 64, 34; 91/513, 519, 520, 525, 530

[56] References Cited

U.S. PATENT DOCUMENTS

| | | | |
|---|---|---|---|
| 2,800,055 | 7/1957 | May | 414/2 |
| 5,014,515 | 5/1991 | Krauter | 92/92 X |
| 5,018,506 | 5/1991 | Danna et al. | 92/92 X |
| 5,019,121 | 5/1991 | Krauter | 92/92 X |
| 5,067,390 | 11/1991 | Negishi | 92/48 |
| 5,079,999 | 1/1992 | Negishi et al. | 92/48 |
| 5,080,000 | 1/1992 | Bubic | 92/48 X |
| 5,107,754 | 4/1992 | Nishikawa et al. | 91/530 |
| 5,317,952 | 6/1994 | Immega | 92/34 X |
| 5,337,732 | 8/1994 | Grundfest et al. | 128/4 |
| 5,385,080 | 1/1995 | Suzumori | 92/171.1 |
| 5,410,944 | 5/1995 | Cushman | 91/530 X |
| 5,474,485 | 12/1995 | Smrt | 92/48 X |

*Primary Examiner*—Hoang Nguyen
*Attorney, Agent, or Firm*—Lappin & Kusmer LLP

[57] ABSTRACT

An apparatus generates power at micro-scale dimensions that is sufficient to simulate the muscle activity required by the joints of robotic fingers. The apparatus includes a bellows device for generating a motion stimulus in response to pressure changes within the bellows. A configuration of programmable micromachined valves is used to regulate the flow of pressurized fluid within the bellows. A microprocessor is responsive to motion commands for controlling the operation of the apparatus. The apparatus is configured as an integrated device that is coupled to the articulations of a robotic hand via suitable attachment mechanisms.

36 Claims, 3 Drawing Sheets

ACTUATORS FOR SIMULATING MUSCLE ACTIVITY IN ROBOTICS

FIELD OF THE INVENTION

The present invention relates to the development of power delivery modules capable of generating force components on a micro-scale dimension and, more particularly, to a microactuator assembly that duplicates muscle activity, particularly those provided in the digital extremities of the human body, thereby facilitating robotic hands, feet and limbs.

BACKGROUND OF THE INVENTION

Many minimally invasive surgical techniques have been and are being developed so that surgery can be performed inside the body with minimal trauma to the patient. Endoscopic surgery, for example, is a medical procedure in which the treatment of internal organs, such as tissue cutting, removal and repair, is performed through a long tube extending through a surgical aperture created in a patient's skin or through a natural orifice of the patient's body. These procedures are accomplished with long thin tools inserted through or contained within the endoscope. Often using a miniature camera attached to the endoscope, the internal surgical field can be observed during the surgical procedure. When performed on the abdominal cavity, the endoscopic system is called a laparoscope and the procedure is termed laparoscopic surgery. When performed on the joints, such as the knee, the endoscopic system is called an orthoscope and the procedure is termed orthoscopic surgery.

These minimally invasive surgical techniques, such as laparoscopic surgery, have received wide acceptance among patients and doctors because of significantly lower incidence of post-operative complications attributable to reduced incision trauma. The benefits of this procedure include quicker recovery times and less patient monitoring, leading to shorter hospital stays and consequent reductions in medical costs. Despite all of these advantages, endoscopic surgery still presents the surgeon with several formidable challenges.

In accordance with current medical practice, certain endoscopic surgical techniques, such as those encountered in laparoscopic and orthoscopic surgery, require the surgeon to operate in a counterintuitive manner that is attributable to the coordination transformation that occurs as the remote end of the endoscope is inserted into and maneuvered within the patient. At present, the surgeon must position and use surgical tools at the remote end of an endoscopic tube, for example in the case of a laparoscope approximately 500 mm long and usually 11 mm in diameter. The tube is moved into position by pivoting it at a fulcrum formed at the point of entry into the patient's skin. This fulcrum pivot requires the surgeon to undertake an inverted sequence of the particular hand motions which would otherwise be appropriate during manual handling of the remote end of the endoscope. For example, if the remote tip inside the body must be moved upward and to the right, the surgeon's hand outside the body must then move downwards and to the left. This mismatch in orientation is further complicated by attempts to coordinate these motions against an image being displayed on a TV monitor, which itself may change in orientation as the camera is rotated. This difficulty represents a major obstacle to widespread use of this surgical method, significantly increasing the actual procedure time for the surgeon.

One example of an endoscopic positioning apparatus used in laparoscopic surgery is disclosed by Begin et al. in "A Robotic Camera for Laparoscopic Surgery: Conception and Experimental Results," *Surgical Laparoscopy & Endoscopy*, Vol. 5, No. 1, pp. 6–11 (1995). Begin et al. propose a robotic surgery system that includes a robotic arm for manipulating a laparoscopic camera. A universal joint is inserted between the end effector of the robotic arm and the camera handler to implement two passive degrees of freedom that prevent arm motions from generating injurious torquing forces that otherwise would develop if the camera was rigidly attached to the robotic arm. The motion of the robotic arm is mathematically represented by three variables to define a spherical displacement model: an alpha angle ($\alpha$) corresponding to the camera orientation (right or left); a beta angle ($\beta$) corresponding to the camera altitude (up or down); and a radius value (R) corresponding to laparoscopic penetration (in or out). Based upon a visual inspection of the operating field acquired by the laparoscopic camera, the image may be reoriented using a computer subsystem that calculates the proper orientation variables $\alpha$, $\beta$, and R for the camera, and then transforms these values into a series of robotic arm motions that are sufficient to produce the desired camera orientation. The robotic arm is instructed to move in accordance with these computed arm motions. However, its operation is limited by the absence of a suitable power delivery system capable of duplicating the muscle activity that controls movement of the human fingers.

Another example of an endoscope positioning apparatus that can be used in laparoscopic surgery is described in copending U.S. patent application Ser. No. 08/525,273, filed by Bruce Nappi and John Coller on Sep. 7, 1995, and entitled Apparatus for Positioning and Moving an Endoscopic Instrument (Attorney's Docket No. LC-6).

In all of these endoscopic systems, the manipulation of the surgical tools provided at the remote end of the endoscope during the surgical procedure is typically accomplished with one or two degrees of freedom, resulting in the necessity of requiring the remote end of the endoscope to be moved around to insure proper positioning of the surgical tools. A system that allows the physician to precisely maneuver surgical tools at the remote end of an endoscope is therefore extremely desirable. Such a system would necessarily involve the robotic manipulation of these endoscopic tools (e.g., the manipulation of robotic fingers attached to an endoscope), and ideally duplicate the movements of the human hand, with all six degrees of freedom, and preferably capable of accomplishing very small micro-manipulative steps with great dexterity.

Generally, robotic assemblies are typically configured with end effectors having a mechanical design which complements the task being executed. For example, a robotic arm may be provided with a gripper hand matched to the contours of its payload. A diverse array of parts can be handled if the robotic arm is fitted with one of a variety of releasable wrist members each designed to support a particular payload. Robotics technology may also be employed to emulate a particular structure of the human anatomy, thus simulating a specified human action.

In applications involving the simulation of a human activity, the structural and operational aspects of the robotics assembly ideally are made to conform to the anatomical features underlying the chosen human capability. Since the human hand is the anatomical structure responsible for producing very precise and controllable motions at small dimensions, robotics research has focused upon designs intended to duplicate the functioning of the human hand, specifically the fingers. For example, the implementation of a prehensile (i.e., grasping) motion involves the use of robotic fingers that simulate the individual phalanx members comprising the digital extremities of the human hand.

By way of background, the mutual linkage of bones in the human skeletal system is accomplished by a connection known as a joint or articulation. In a movable articulation, the joint is formed by the coupling of two contiguous bony surfaces whose articular extremities are covered by cartilage and connected together by ligaments consisting mainly of bundles of white fibrous tissue. A physical structure modeled after such a connection is well known in the art, e.g., an interconnection of robotic fingers imitating the digital extremities of the human hand. In general, robotics research has succeeded in developing devices that structurally reproduce the physical aspects of the phalangeal articulations. For example, the Utah-MIT robotic hand and the Salisbury robotic hand are representative of robotic structures having multi-jointed fingers that can emulate the grasping ability of a human hand.

A precise robotic reproduction of the human hand requires not only that the physical structure be emulated, but also that the robotic fingers function with the same characteristic motion demonstrated by human fingers. Although current robotic assemblies show great promise for moving workpieces within the geometrical space of manufacturing environments, existing limitations prevent the development of workable prehensile end effectors which are specifically adaptable to the precise maneuvering of instruments at micro-scale dimensions. The principal challenge involves the design of an adequate, yet inexpensive control apparatus capable of manipulating the robotic fingers so that they fluidly and precisely emulate the motions permitted by the phalangeal joints, i.e., both flexor and extensor motions. In particular, the desired degree of precision requires a control apparatus that can perform the muscle activity needed to implement the joint motion. This search for a control apparatus capable of delivering sufficient power to simulate the muscle activity is made even more difficult by the need to produce such power on micro-scale dimensions. One useful design approach that addresses this problem involves identifying the anatomical structures responsible for joint motion and then constructing an apparatus which emulates the identified structure, as described below.

The anatomical motions permitted by the joints are controlled by a network of muscles whose connection with the bones and cartilage is accomplished either directly or indirectly through the intervention of fibrous structures called tendons. Accordingly, the relevant anatomical structure for purposes of designing such a robotic power delivery system is the muscle and tendon group that interconnects the phalanx members (i.e., fingers) at the digital extremities of the upper human torso. A need therefore exists to manufacture a suitable robotic system for simulating the muscle activity at the finger joints of the human hand, and which is particularly useful in the manipulation of surgical instruments.

Achieving large forces and small motions in a small volume with a robotically controlled hand has always been a formidable and complex task. The problem becomes even more complicated as additional fingers and joints are included to increase the dexterity and therefore expand the range of motion and degree of control with multiple degrees of freedom. Nevertheless, the employment of a multifunctional tool is desirable because it provides an opportunity for eventually reducing the number of individual tools required to complete any task. Therefore, for each application, the selection of an appropriate robotic power delivery system to deliver adequate motive energy is a significant task. The principal technologies currently in use include linkages, "tendons" and electric motors.

Linkages are often used in robotic hands designed for limited degrees of freedom (e.g., single fingers with one or two joints), and may be configured as push rods and rotary shafts. Although additional degrees of freedom are possible with more rods, each additional rod imposes a dimensional reduction upon its size, where dimensions are constrained as in the remote end of an endoscopic tool. In particular, since the system design typically requires that the overall envelope dimensions remain the same, an increase in the number of rods decreases the available rod diameter. This reduces the ability of each rod to transmit power. Accordingly, linkage mechanisms are not suitable for applications where power must be transferred to tools which require even a modest number of degrees of freedom.

"Tendons" are the most commonly used means of power and control delivery in robotic hands, and are typically configured as single strands of wire which substantially reproduce the tendon structure in human hands. Tendons represent a suitable structure for delivering robust quantities of power from one location to another, particularly in combination with sheaves, bellcranks, and other such devices which allow the tendons to support a wide range of motion over a considerable distance. However, tendon structures are limited because they must be powered by an assembly of power sources such as motors which are currently unacceptably large for the desired micro-scale applications. Each moving element requires an individual tendon and power source. Due to their relatively large size, the actuators are typically assembled into a large package located remote from the element they actuate, requiring a very long tendon to transmit the necessary force.

Electric motors offer numerous advantages such as relatively low cost, availability as a stand-alone operating unit, and amenability to installation and direct integration with electronic controllers. However, conventional miniature electric motors simply cannot provide adequate power for the vast majority of robotic systems such as those that must rapidly maneuver a surgical instrument grasped by a robotic hand. Instead, electric motors are primarily used in applications where very low motive force is required, e.g., when slow robotic finger movement is acceptable.

In summary, conventional power delivery systems are inadequate for the operations needed in small-scale robotics applications. Recently, however, power delivery systems using fluidics have received attention. The use of fluids to deliver power is attractive because of their ability to produce high motive energy and their capacity for deployment in a diverse range of applications.

Fluid power has traditionally been used in large-scale applications, such as with cranes and construction equipment. Fluidic systems have also been employed in small-scale operations, including machine automation, grasping fixtures, and diverting workpieces on conveyor belts. However, fluid-based approaches are often passed over for robotic designs because the auxiliary equipment needed to generate and deliver adequate fluid flows is larger than electrical systems. There is also a reluctance to use fluid power in sterile conditions such as surgical operating facilities, primarily because fluids are considered messy and may be difficult to contain due to their rapid diffusion, creating a risk of compromising the integrity of the operating room and possibly infecting the patient. Furthermore, since many robotic systems are usually designed by electronic and computer engineers, many of the robotic designers are less familiar with the field of fluidics.

Certain hydraulic devices for delivering energy to remote sites of reduced dimensions for accomplishing a surgical procedure nevertheless have been suggested. These configurations have generally used a bellows or piston-like element to transform hydraulic power into a motion stimulus for moving tools or instruments. Examples of such bellows configurations are set forth below.

In one conventional configuration, the bellows is used to impart an axially reciprocating motion that alternately advances and retracts a work element coupled to the bellows. U.S. Pat. No. 3,884,238 to O'Malley et al. discloses a bellows responsive to the alternate application of compressed air and vacuum pressure for creating a reciprocating motion that axially translates a telescoping tube. The tube is fitted with a sharpened edge for cutting diseased tissue, facilitating the removal of cataracts during eye surgery. U.S. Pat. No. 4,986,827 to Akkas et al. employs a diaphragm assembly (i.e., bellows device) in a similar manner, imparting a reciprocating motion to a cutting instrument. U.S. Pat. No. 5,024,652 discloses an ophthalmological resection device employing a hydraulic system (i.e., bellows and hydraulic pipe) that is responsive to depressions of a surgeon-operated foot pedal to actuate the bellows, causing the bellows to develop a reciprocating linear motion within a cutting tool that effects the removal of tissue from a body cavity. U.S. Pat. No. 5,217,465 to Steppe describes a flexible and steerable aspiration tip that is suitable for microsurgical procedures. Specifically, the aspiration tip is configured with a bellows adapted to reciprocate within a chamber in response to pneumatic pressure changes, thereby supplying a linear motion which translates the tip between its flexor states. U.S. Pat. No. 5,314,408 to Salmon et al. discloses a vascular catheter system configured with an axially expandable member (i.e., bellows) for reciprocatably advancing or retracting a workpiece (e.g., ultrasonic transducer) attached to the distal end of the catheter body.

In another category of bellows configurations, the bellows is used to adjust the position of an attached work piece. For example, in U.S. Pat. No. 2,800,055 to May, a hand control unit is equipped with a telescopic control lever whose motions produce either a discharge or injection of pressurized fluid within the bellows assembly. The resulting bellows movement displaces an array of blocks that subsequently exert a force against a holder mechanism carrying a surgical instrument. U.S. Pat. No. 4,946,329 to Krueger similarly discloses a micromanipulator for making precise, reproducible adjustments to the position of a mechanical element. Specifically, an hydraulically-operated bellows member is placed in operative engagement with a lever arm secured to a platform. Motion of the bellows member produces microadjustments to the platform, thereby maneuvering a microtool supported by the platform.

In yet another hydraulic system based upon bellows, U.S. Pat. No. 4,056,095 to Rey et al. discloses a control device implantable in a sub-cutaneous region and actuated by pressure applied to the overlying skin. The control device includes a set of coaxially-disposed bellows adapted at respective ends for hydraulically communicating with a fluid chamber and with an inlet-outlet port serving as a nozzle for a flexible duct (e.g., an artificial sphincter muscle). As pressure is applied to the skin, fluid from the chamber is forced into the bellows arrangement to create a reciprocating motion that communicates pressure changes through the inlet-outlet, causing the flexible duct to alternately open or close. Hence, the bellows arrangement is useful in actuating an artificial duct which itself defines the passageway into an intra-corporal orifice (e.g., a bladder).

Although the bellows configurations described above have uses at relatively small dimensions, including, inter alia, the resection of diseased tissue, adjusting the position of a workpiece, and actuating artificial ducts, none of the cited configurations can simultaneously produce precisely controlled motions and relatively high force, and do so without an external fluid control system in small enough size to replicate a human hand with no auxiliary motor assembly. Additionally, each bellows element of conventional use requires a separate fluid line. It is clear that the current state of bellows development has not embraced an integrated solution for providing power on a miniature scale sufficient to manipulate surgical instruments with dexterity with many degrees of freedom.

OBJECTS OF THE INVENTION

It is a general object of the present invention to obviate the above-noted and other disadvantages of the prior art.

It is a more specific object of the present invention to provide a microactuator assembly that integrates a bellows device with a configuration of micromachined valves operated by an integrated control unit to emulate a small muscle capable of both flexor and/or extensor motions.

It is a further specific object of the present invention to provide a microactuator assembly adapted for use as a micromuscle simulator to duplicate the muscle activity at a finger joint.

And another object of the present invention is to provide a system of robotically controlled microactuator assemblies capable of being grouped together to achieved dexterous motions through many degrees of freedom.

Other objects of the invention will in part be obvious and will in part appear hereinafter. The invention accordingly comprises the apparatus possessing the construction, combination of elements, and arrangement of parts which are exemplified in the following detailed disclosure, and the scope of the application of which will be indicated in the claims.

SUMMARY OF THE INVENTION

The foregoing and other objects will be achieved by an integrated apparatus for generating a motion stimulus, wherein the apparatus comprises:

bellows means, responsive to a pressure condition at an input port thereof, for generating a motion stimulus;

valve means, integrally coupled to the bellows means, for operatively regulating the application of pressure to the input port of the bellows means; and integral controller means for controlling the operation of the valve means.

The apparatus further comprises a pressure generation means for generating the pressure. The pressure generation means includes a source means for generating a flow of pressurized fluid, and a vacuum means for generating a vacuum pressure.

The valve means includes a first selectively operable micromachined valve adapted to admit the flow of pressurized fluid from the source means into the bellows means; and a second selectively operable micromachined valve coupled to the vacuum means and adapted to withdraw pressure from the bellows means.

The controller means includes a microcomputer.

The apparatus further comprises detection means, in motion-detecting relationship with the bellows means, for detecting a position of the bellows means; and feedback means, responsive to the detected position of the bellows means and a position command signal from the microcomputer that is representative of a selected position of the bellows means, for adjusting the operation of the valve means.

According to another aspect of the present invention, in a robotic system including a configuration of robotic fingers, an integrated actuator assembly is coupled to the robotic fingers for displacing the robotic fingers, wherein the assembly comprises:

bellows means for generating a motion stimulus as pressurized fluid flows through an input port thereof;

valve means, in fluid communication with the input port of the bellows means, for controllably regulating the fluid flow through the input port of the bellows means; and controller means, coupled to the valve means, for controlling the operation of the valve means.

The valve means includes a configuration of programmable micromachined valves. The controller means includes a microprocessor.

BRIEF DESCRIPTION OF THE DRAWINGS

For a fuller understanding of the nature and objects of the present invention, reference should be had to the following detailed description taken in connection with the accompanying drawings, wherein.

The same or similar elements throughout the drawings are identified with the same reference numeral.

DETAILED DESCRIPTION OF THE DRAWINGS

In its most general form, the present invention is directed to an apparatus for precisely delivering motive power at micro-scale dimensions. The apparatus includes a power source capable of controllably transmitting power and further includes an actuator element for translating power from the power source into the required motion stimulus. In accordance with one aspect of the present invention, the power is transmitted through a fluid and the actuator element is a bellows device which expands and contracts in response to fluid provided to and withdrawn from the bellows device so as to simulate muscle activity (both flexor and extensor motions). More particularly, the apparatus includes a microactuator assembly utilizing a bellows device to convert a fluid under pressure (e.g., pneumatic or hydraulic, although a non-compressible hydraulic fluid is preferred), provided from a pressurized fluid source, into a force component. An integrated valve mechanism is used to regulate the pressure being introduced into or withdrawn from the bellows device, while an integrated control unit is employed to direct the operation of the apparatus.

In accordance with another aspect of the invention described in greater detail hereinafter, each valve mechanism can be selectively controlled by the control unit so that plural valves and the corresponding set of bellows can be used with a minimal one pressure fluid line, and one control bus connected to all of the control units.

Figure 1:
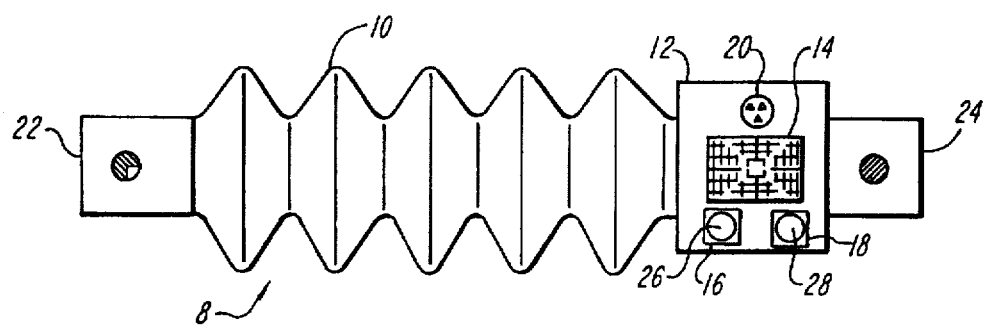
FIG. 1 is a schematic illustration of a microactuator assembly in accordance with the present invention.

Referring to FIG. 1, microactuator assembly 8 in accordance with the present invention includes a bellows device 10 and controller 12. The controller 12 preferably includes a microprocessor controlled circuit 14 in the form of an integrated circuit for controlling the two micromachined valves, indicated generally at 16 and 18. The valves respectively regulate the flow of fluid between bellows 10 and the pressure ports 26 and 28 which are respectively adapted to provide pressurized fluid to and receive discharged fluid from bellows 10 through the corresponding valves 16 and 18. Each valve is normally closed. Circuit 14 is provided with unique programmable addresses for the corresponding valves 16 and 18 so that when a signal representative of one of the unique addresses is applied to the input of the circuit 14, the corresponding valve will open. The circuit 14 also controls the length of time the valve is open so as to control the length of extension of the bellows 10, as will be more evident hereinafter. Circuit 14 receives address and control signals via electrical connector 20 that is coupled to other circuits 14 of other microactuator assemblies using an appropriate bus connection, as will be more evident from FIG. 5 described hereinafter. Bellows 10 is configured with linking mechanisms 22 and 24 secured at respective ends thereof to facilitate attachment to other devices, such as articulated elements of a robotic finger provided to the end of an endoscope.

Bellows 10 performs the required actuator function which involves the conversion of fluid pressure into a force component. As used herein, "fluid" refers generally to a substantially incompressible substance characterized by relatively rapid diffusion. The fluid is preferably a liquid component creating a hydraulic pressure, although in some instances where the fluid can be compressible, the fluid can be a gas component creating a pneumatic pressure. This device offers numerous advantages, particularly as a component in medical applications. For example, as discussed below, the automation of endoscopic or laparoscopic surgery requires an actuator device capable of preserving the integrity of the operating room, which makes the bellows an appropriate device for implementation because it is inherently leak proof, possesses low friction and hysteresis, and does not require any sealing material.

In general, bellows 10 defines a sealed enclosure having accordion-like walls that permit the bellows to be axially expanded and contracted, allowing the volume within the enclosure to be varied in response to fluid pressure changes within the sealed enclosure. The bellows is configured with an inner chamber disposed along its longitudinal dimension, and is operationally characterized by a reciprocating motion as the fluid pressure changes within the chamber. The inner chamber is configured as a cylindrically-shaped chamber that is adapted to receive a flow of pressurized fluid during an expansion mode, and to discharge the pressurized fluid during a contraction mode. Depending upon the placement of the chamber relative to the outer circumference of the bellows, the direction of thrust will vary accordingly. FIGS. 2 and 3 are schematic diagrams of individual bellows devices used to develop a linear and pivoting motion, respectively.

Figure 2A:
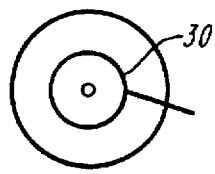
FIG. 2A is a cross-sectional axial view of a bellows device in accordance with one aspect of the present invention.
Figure 2B:
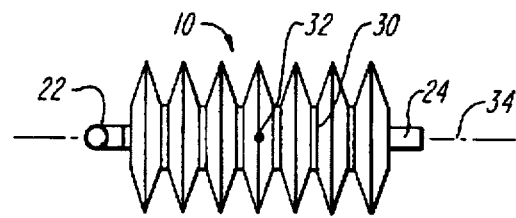
FIGS. 2B and 2C schematically illustrate the compressed and extended phases, respectively, of the bellows device represented in FIG. 2A.
Figure 2C:
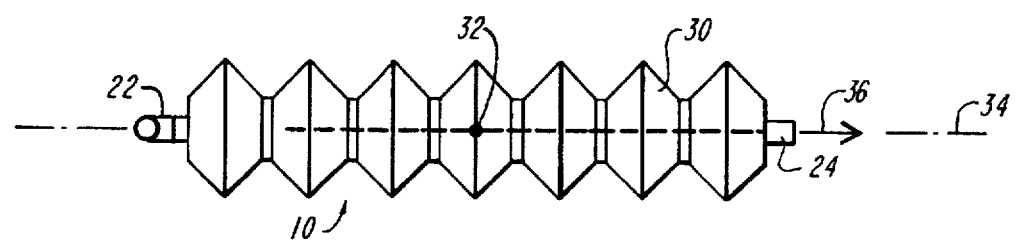

Referring to FIG. 2A, a cross-sectional view is shown along the axial dimension of a bellows device which produces a linear thrust during its reciprocating expansion and contraction motion. To achieve such thrust, the bellows is configured with an inner chamber 30 disposed concentrically in relation to the outer circumference of the bellows. Specifically, the center point 32 of the chamber 30 is coincident with the longitudinal axis 34 of the bellows. When withdrawing fluid from the chamber 30, the bellows will exhibit the contracted form shown in FIG. 2B. As pressurized fluid is introduced into the bellows chamber 30, the bellows becomes extended as shown in FIG. 2C, exerting a linearly-directed thrust in the direction of the arrow 36 along the axis 34. The linear extension is specifically attributable to the concentric positioning of the chamber with respect to the bellows circumference and additional guiding means (not shown). When fluid is withdrawn from the chamber, the bellows will contract due to the spring nature of the bellows or an auxiliary spring (not shown), producing a linear force in the opposite direction of arrow 36.

Figure 3A:
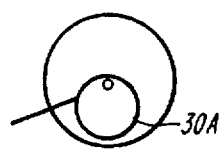
FIG. 3A is a cross-sectional axial view of a bellows device in accordance with another aspect of the present invention.
Figure 3B:
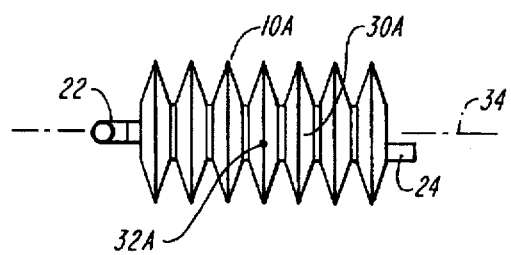
FIGS. 3B and 3C schematically illustrate the compressed and extended phases, respectively, of the bellows device represented by FIG. 3A.
Figure 3C:
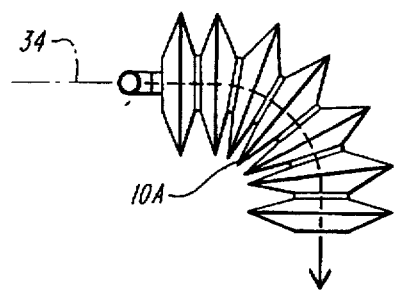

Referring to FIG. 3A, a cross-sectional view is shown along the axial dimension of a bellows 10A which produces a rotational or pivoting thrust during its reciprocating motion. The bellows is configured with an inner chamber 30A whose center point 32A is displaced away from the longitudinal axis 34 of the bellows and towards the outer circumference. The inner chamber is therefore offset from the concentric placement depicted by the bellows of FIGS. 2A-C, which illustrates a linear reciprocating motion. When contracted, the bellows will take a form resembling that depicted in FIG. 2C. However, by offsetting the inner chamber in the manner described, the bellows 10A will follow the curved or rotational motion depicted in FIG. 3C when pressurized fluid is introduced into the bellows chamber. The consequent thrust generated by this bellows during its extension mode provides both a power and bearing function.

Although the bellows device disclosed herein is represented as a diaphragm element, this representation is shown for illustrative purposes only and should not serve as a limitation of the present invention. Rather, it should be apparent to those skilled in the art that other devices may be used, such as a piston-like cylinder, without departing from the basic operation of the microactuator assembly.

The transmission of fluid into and away from bellows 10 or 10A is regulated by a valve mechanism. In a preferred implementation, this valve mechanism is configured with micromachined valves capable of supporting microflow transmissions. These valves are adapted to be in fluid communication with the inner chamber of the bellows, depending upon the selected fluid medium. The NC-1500 Fluistor™ Microvalve from Redwood Microsystems is one example of a suitable valve mechanism. This normally closed gas valve operates upon the principle that heating a gas will cause the gas to expand; accordingly, if the gas volume is held constant, the gas pressure will increase as heat is applied. The pressurized gas can then be used to move a diaphragm, allowing it to function as a valve gate for controlling the flow of fluid. The valves are further adapted for hydraulic communication with input port 26 and drain port 28 to create a bidirectional fluid flow between bellows 10 or 10A and a hydraulic source facility (discussed below) coupled to ports 26 and 28. In particular, when the device is programmed for positive linear thrust (i.e., during the expansion mode of bellows 10 or 10A), the valves are adapted to receive hydraulic fluid from the hydraulic source facility through input port 26, and then direct this fluid into the bellows chamber. Alternatively, during the contraction mode of bellows, the valves are operable to direct hydraulic fluid being discharged from the bellows into the hydraulic source facility through drain port 28.

Figure 4:
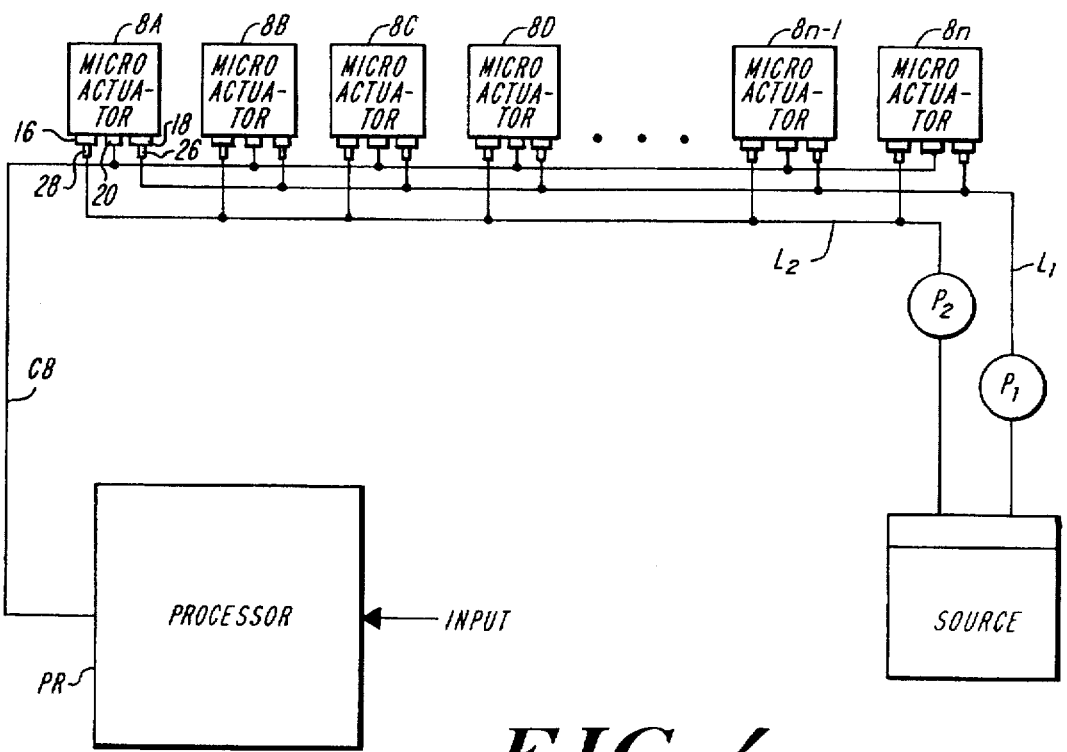
FIG. 4 is a block diagram of the preferred system comprising a plurality of microactuator assemblies connected together with a common control bus and hydraulic lines for delivering liquid to and from the bellows of each assembly.

As mentioned above and as illustrated in FIG. 4, the input port 26 is coupled to a hydraulic source facility of higher pressure than ambient pressure, indicated by $P_1$, that provides hydraulic fluid to input port 26, while the drain port 28 is coupled to a facility of lower pressure than ambient pressure, indicated by $P_2$, so that it draws hydraulic fluid from drain port 28. It is noted that the facilities $P_1$ and $P_2$ can be pumps connected to the same source of hydraulic fluid indicated at S in FIG. 4. The facilities $P_1$ and $P_2$ can be connected to the respective input and drain ports 26 and 28 of each microactuator assembly 8 through respective feed lines $L_1$ and $L_2$, each fitted with an array of taps hydraulically coupled to the respective port of a corresponding microactuator assembly 8. This parallel architecture allows hydraulic fluid to be simultaneously and independently supplied to all, a subset, or a single one of the bellows devices. The hydraulic fluid in line $L_1$ must be maintained at a sufficient pressure as provided by facility $P_1$ such that the pressurized hydraulic fluid is constantly presented to all of the input ports 26. The line $L_2$ is likewise maintained at a pressure sufficiently below ambient pressure so that any of the bellows of the assemblies 8 can be quickly drained of at least a part of any hydraulic fluid within the bellows through the corresponding drain ports 28. Finally, a separate processor PR, for example a computer system, is connected to each of the assemblies through a common bus CB. Each assembly is provided with a unique address. The processor PR provides both an address and control signal to each assembly over the bus so that each assembly is separately controlled. Each control signal provides the appropriate information of how much the bellows of a particular assembly should be extended or contracted from its current position. This parallel architecture allows all of the bellows of the assemblies 8 to be simultaneously and independently controlled. This parallel architecture among the actuator assemblies 8 minimizes construction complexity and cost, and is amenable to the addition of further actuator assemblies through their attachment to any available drain and supply taps along the appropriate feed lines and connection to the control bus CB.

In accordance with one alternative aspect of the present invention, each actuator assembly 8 can be designed to have a local intelligence capability that permits it to analyze motion requests from other actuator assemblies and to generate its own commands. In this instance the processor PR would be partially used, or not used to perform the control function for the entire array of actuator assemblies.

As described below in connection with FIG. 5, this local intelligence is embodied in circuit 14 and comprises a very large-scale integrated (VLSI) circuit chip including a receiver demultiplexer (DMUX) 40 for receiving commands addressed to the actuator assembly. Processor 14 further includes microprocessor 42 for analyzing and responding to the commands, preferably in conjunction with a memory unit that furnishes a matrix of appropriate responses. An analog servo control circuit 44 is also provided for controlling the valves, hence regulating the transmission of hydraulic fluid into the bellows. A position sensor 46 operates in a feedback loop with servo system 44 to provide position information to microprocessor 42.

Figure 5:
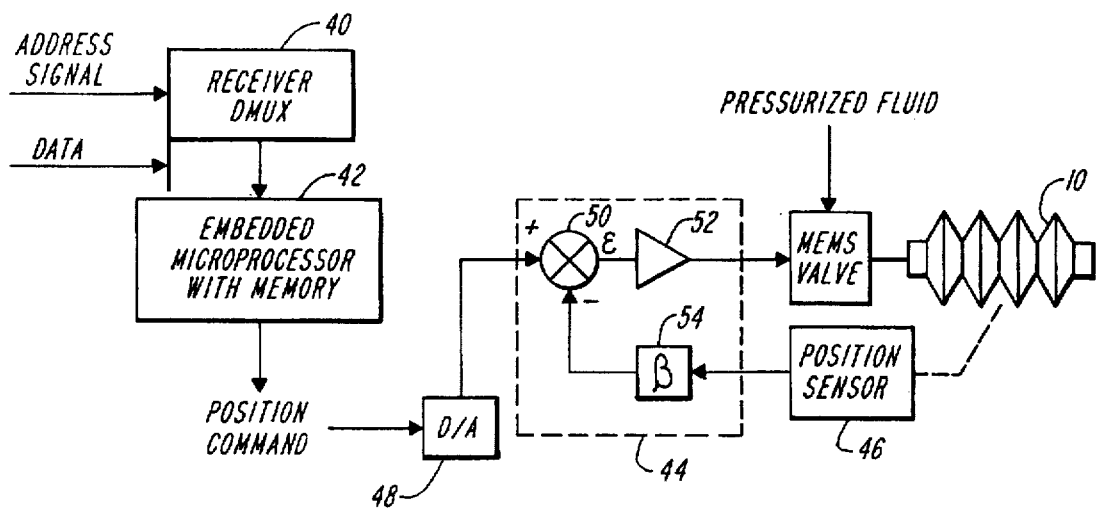
FIG. 5 is a block diagram depicting the functional components of the microactuator assembly of FIG. 1, in accordance with a preferred embodiment of the present invention.

Referring to FIG. 5, a block diagram is shown of the electronic control apparatus embodied in circuit 14 of each actuator assembly. The receiver DMUX 40 receives address and data signals (representative of power or force, or a position of the bellows) from the common bus CB which are applied to the circuit 14 through connector 20 (see FIG. 1). Comparing the address signal and the address of the assembly 8 (which can be stored in the memory of the microprocessor 42), if a match is made the data signal is decoded by DMUX 40 and forwarded to the microprocessor 42.

The microprocessor 42 analyzes the data and determines an appropriate course of action. For example, when the data represents a command to operate bellows 10 in a particular manner (e.g., in a contracted or expanded state), it is necessary to determine whether such an operation falls within the range of valid and permissible actions of the bellows. This determination may be facilitated by a memory unit provided with microprocessor 42, which includes a table of appropriate responses each indexed to a respective command. By accessing the memory upon receiving a command, the microprocessor will formulate a reply in accordance with the response retrieved from memory. This reply may take the form of a denial of the requested operation, or acceptance of the request followed by its execution.

In the event that the bellows is to be activated, either in response to a request from another actuator assembly or in response to a self-directed command provided by the actuator assembly itself, or a signal provided by the processor PR, the current position of the bellows is determined, and compared to the desired position requested by the data signal. Based on this comparison, an appropriate position command is generated to initiate activation of the bellows. The digital position command is converted by a digital-to-analog (D/A) converter 48 into an analog signal representation. This conversion is necessary in the embodiment described because the servo feedback loop and the valves are responsive to analog signals.

The analog position command is applied to an analog servo control circuit 44 that operates a closed-loop feedback function to ensure proper activation of bellows 10. The position command is applied to the positive reference port of a differential summer 50 where it is combined with the feedback signal appearing at the negative reference port. The differential summer 50 provides an error signal ∈ that is amplified by amplifier 52 and then forwarded to the valves as a control signal representative of the degree of flow control that the valves are to exercise over the pressurized fluid. Hence, the control signal reflects the amount of hydraulic fluid to be admitted into or withdrawn from bellows 10 so that the bellows moves to the desired position. Obviously, if the bellows is already in the desired position the control signal will indicate that no change is necessary.

A position sensor 46 continuously monitors and detects the position of a reference point on bellows 10 and provides a position indicator representative of this detected position. The position indicator is scaled by a gain constant of value β using a feedback scaler 54. The scaled signal is applied to the negative reference port of differential summer 50 as the feedback signal. As shown, a feedback path is formed by position sensor 46 and feedback scaler 54. The analog servo control circuit 44 continues to operate until the error signal is optimized, indicating that bellows 10 is now in its desired position.

As described above, when each actuator assembly is equipped with its own microprocessor, a number of operational advantages can be provided. By distributing the computer power of the entire system into individual microprocessors each independently operable and self-administrating, multiple tasks may be run in parallel. This concurrent processing improves the adaptive response of the system and reduces 8 the computation period needed to implement a specified operation since each actuator is only responsible for monitoring its own environment. Conventional systems are characterized by completely relying on remote processing, in which a central computer performs all of the processing for all actuator assemblies. Consequently, the signal paths to the actuator assemblies can be quite lengthy, limiting the communications to low bandwidth signals. As a result, conventional actuators exhibit very slow operating speed, an unacceptable feature especially where fast, precise motions are needed. By contrast, the local processing within each actuator assembly of the present invention eliminates any concern over unduly long communication paths, allowing the transmission of high bandwidth signals to create a faster, more responsive system. The availability of high bandwidth feedback to servo system 44 results in a faster convergence of the bellows movement to its desired position.

The local processing also permits each actuator assembly to receive commands from a number of different locations. This allows construction of a redundant system in which each actuator assembly can function as a system supervisor to monitor the overall system operation and even to assume complete control in the event that a system failure disables the processing capability of all other actuator assemblies.

In accordance with another aspect of the present invention, circuit 14 serves as a common platform to facilitate the monolithic integration of the microactuated valves and the electrical control apparatus. This integration may be established using a single silicon wafer as the platform. Additionally, the entire actuator assembly is preferably configured as an integrated device by packaging circuit 14, connector 20, and the hydraulic fluid ports 26 and 28 onto a single embedded platform represented by controller 12, which is then directly integrated with bellows 10.

As noted above, current robotics technology includes finger elements that structurally emulate the phalangeal articulations comprising the digital extremities of the human hand. However, their operation is severely limited by the absence of a suitable power system capable of duplicating the muscle activity that controls movement of the human fingers. The actuator assembly according to the present invention represents a significant technological advance in delivering precise, high-intensity power at micro-scale dimensions, and therefore may serve as an integral feature of robotics systems, as discussed below.

Several elements of the actuator assembly disclosed herein constitute analogues of certain anatomical features within the human body that are responsible for muscle activity. In particular, the pressurized hydraulic fluid applied to bellows 10 corresponds to an arterial blood flow that provides oxygenated blood to the muscle tissue. Therefore, the fluid being discharged from bellows 10 corresponds to the de-oxygenated venous blood flow leaving the muscle tissue. Additionally, the microcomputer within circuit 14 provides the electrical signals sufficient to activate and control the bellows motion, functioning similarly to the nervous system that supplies the impulse energy needed to excite the cells of the muscle tissue. Accordingly, the integrated actuator assembly of the present invention exhibits operating characteristics that make it suitable for deployment as a micro-muscle simulator, hence serving as an enabling technology for designing miniature modular muscles useful in robotic applications.

Figure 6:
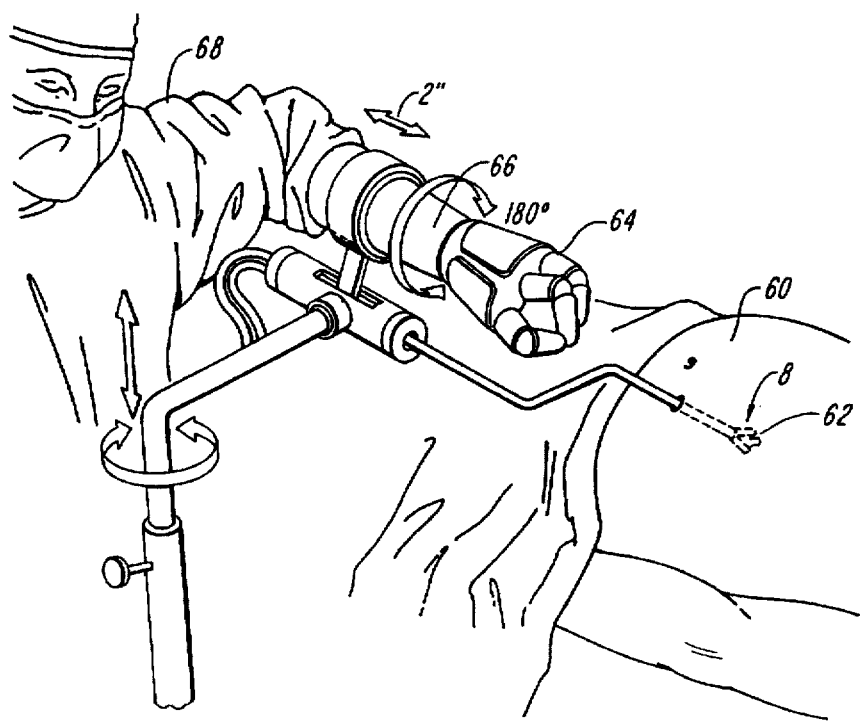
FIG. 6 shows a pictorial view of an endoscope designed in accordance with the present invention and shown in use.

In accordance with a preferred embodiment of the present invention, the actuator assembly disclosed herein is adapted for use as the elemental building block in manufacturing micro-muscle simulators. Specifically, the actuator assembly functions as a suitable power control system for reproducing the muscle activity needed to flex the robotic finger joints. This adaptation is illustrated in FIG. 6, wherein a surgical robot robotically performs laparoscopic examinations on a subject patient indicated at 60. The robot includes a miniature, three-fingered hand 62 whose finger joints are powered by a plurality of microactuator assemblies 8, each of which functions as a micro-muscle simulator. A control glove 64 is worn by the surgeon 68 to control the movement of the robotic fingers. A visualization system (not shown) is preferably used by the surgeon to monitor the surgical field inside the patient.

Based upon an analysis of the maneuvers undertaken by a surgeon to perform endoscopic procedures, a three-fingered robotic hand is believed to be adequate to substantially simulate the functions of the human hand. A repeater device (not shown) is used as an interface between the surgeon and the robotic hand, functioning as a control apparatus that is responsive to input data provided by a surgeon for generating motion commands that activate the robotic hand. The repeater device simply transmits (i.e., repeats) the motion components that are generated by the surgeon, without any intermediate coordinate transformation or motion analysis. In a preferred implementation, the repeater device is configured as an exoskeletal or glove controller 66 that is adapted to receive the hand of a surgeon, who then manipulates the fingers of the glove to effect endoscopic positioning.

Position detectors (not shown) are disposed on the glove to measure the orientation of each joint of the hand. When it becomes necessary to maneuver the endoscope, the surgeon moves the fingers of the glove controller in the desired fashion. This motion is detected by the position detectors as orientation values, which are encoded by a command signal generator and supplied to the array of actuator assemblies. These control signals are decoded and transferred to the appropriate actuator assemblies to simulate a muscle activity that moves the robotic fingers. The command signals, in particular, control the motion of a corresponding joint in the robotic hand located within the patient's body.

The robotic hand is essentially a miniaturized, scaled-down version of the glove controller, and is mechanically coupled to the endoscopic instrument such that movement of the robotic fingers is directly communicated to the instrument as functionally equivalent displacement vectors. This motion within the robotic fingers is created by an array of micro-muscle simulators (i.e., actuator assemblies) each responsible for the motion of a particular joint. The actuator assemblies are coupled via their linkage mechanisms 22 and 24 (see FIG. 1) to respective articulations of a robotic finger. Upon receiving a motion command (which is carried on the lines in FIG. 5), the actuator assembly will respond and activate the bellows, producing a force component that is communicated to the robotic finger joints. For example, if a bending motion is requested of the forefinger, the appropriate bellows devices will be operated in their contraction modes.

By using such a glove-type controller to drive a geometrically identical but miniaturized robotic hand, the design of the robotic hand need not be constrained by concerns over whether the robotic hand will be issued a series of geometrically illegal motion commands related to inter-finger motion. Even if the robotic hand possesses degrees of freedom in its fingers and joints that do not have counterpart human motions, the use of the surgeon's finger movements as the source of all motion commands to the actuator assemblies means that the glove controller cannot issue a set of commands which violate the finger geometry constraints. Stated otherwise, the anatomical limitations governing the range of movement within the human hand are the same limitations experienced by the robotic hand. If a sequence of switches were used to control each of the finger joints, for example, the process of determining finger interference would be a major calculational task since activation of the switches does not reflect actual human motions.

What has been shown and described herein is a novel apparatus capable of delivering force components at microscale dimensions. The apparatus is configured as an actuator device that converts a pressure signal (i.e., a pneumatic or hydraulic fluid flow) into a power signal sufficient to displace objects at this dimensional level. A bellows is provided to perform the actuator function, while an arrangement of programmable micromachined valves is used to regulate the flow of pressurized fluid through the bellows. A microprocessor controls the operation of the apparatus. In a preferred configuration, the elements of the apparatus are assembled onto an integrated platform. The operating features of the apparatus make it well-suited for deployment in a robotics application, functioning as a micro-muscle simulator to provide adequate power for simulating the muscle activity required by the joints of robotic fingers.

Since certain changes may be made in the above apparatus and method without departing from the scope of the invention herein described, it is intended that all matter contained in the above description or shown in the accompanying drawings shall be interpreted in an illustrative and not in a limiting sense.

What is claimed is:

1. An integrated apparatus for generating a motion stimulus, said apparatus comprising:

a base;

bellows means, at least partially integrally coupled to said base and responsive to a pressure condition at an input port of said bellows means, for generating a motion stimulus;

valve means, at least partially formed within said base and integrally coupled to said bellows means, for operatively regulating the application of pressure to the input port of said bellows means; and a controller means, at least partially formed within said base, for controlling the operation of said valve means.

2. The apparatus as recited in claim 1, further comprising pressure generation means for generating said pressure.

3. The apparatus as recited in claim 2, wherein said pressure generation means comprises:

source means for generating a flow of pressurized fluid; and vacuum means for generating a vacuum pressure.

4. The apparatus as recited in claim 3, wherein said source means generates a pneumatic fluid flow.

5. The apparatus as recited in claim 3, wherein said source means generates a hydraulic fluid flow.

6. The apparatus as recited in claim 3, wherein said valve means comprises:

a first selectively operable micromachined valve adapted to admit the flow of pressurized fluid from said source means into said bellows means; and a second selectively operable micromachined valve coupled to said vacuum means and adapted to withdraw pressure from said bellows means.

7. The apparatus as recited in claim 3 wherein said valve means comprises a micromachined valve adapted to be selectively coupled to said source means for admitting the flow of pressurized fluid from said source means into said bellows means, or coupled to said vacuum means for withdrawing pressurized fluid from said bellows means.

8. The apparatus as recited in claim 3, further comprising:
a fluid supply port for coupling said source means to said valve means; and
a fluid drain port for coupling said vacuum means to said valve means.

9. The apparatus as recited in claim 1, further comprising connector means for providing data signals and power signals to said controller means, wherein said data signals are representative of a desired movement of said bellows means.

10. The apparatus as recited in claim 1, wherein said controller means comprises a microcomputer.

11. The apparatus as recited in claim 10, further comprising:
detection means, in motion-detecting relationship with said bellows means, for detecting a position of said bellows means; and
feedback means, responsive to the detected position of said bellows means and a position command signal from said microcomputer that is representative of a selected position of said bellows means, for adjusting the operation of said valve means.

12. The apparatus as recited in claim 1, wherein said bellows means is configured to generate a substantially linear thrust.

13. The apparatus as recited in claim 1, wherein said bellows means is configured to generate a substantially non-linear thrust.

14. The apparatus as recited in claim 13, wherein said substantially non-linear thrust includes a rotational motion component.

15. A robotic system comprising:
at least one robotic movable member; and
an integrated actuator assembly coupled to said robotic movable member for moving said robotic movable member, said integrated actuator assembly comprising:
a base,
bellows means for generating a motion stimulus as pressurized fluid flows through an input port thereof,
valve means, at least partially formed within said base in fluid communication with the input port of said bellows means, for controllably regulating the fluid flow through the input port of said bellows means, and
controller means, at least partially formed within said base and coupled to said valve means, for controlling the operation of said valve means.

16. The robotic system as recited in claim 15, wherein said bellows means is operable in an expansion mode to create thrust in a first direction to move said robotic movable member as pressurized fluid is admitted into said bellows means, and operable in a compression mode to create thrust in a second direction opposite to said first direction to move said robotic movable member as pressurized fluid is withdrawn from said bellows means.

17. The robotic system as recited in claim 15, wherein said bellows means is configured to generate a substantially linear motion stimulus to move said robotic movable member.

18. The robotic system as recited in claim 15, wherein said bellows means is configured to generate a substantially curvilinear motion stimulus to move said robotic movable member.

19. The robotic system as recited in claim 15, further comprising:
fluid supply means, coupled to said valve means, for supplying a flow of pressurized fluid to said valve means; and
fluid reservoir means, coupled to said valve means and maintained at a pressure sufficient to withdraw fluid from said bellows means and then through said valve means, for receiving fluid withdrawn from said bellows means.

20. The robotic system as recited in claim 15, wherein said valve means comprises a configuration of programmable micromachined valves.

21. The robotic system as recited in claim 15, wherein said controller means comprises a microprocessor.

22. The robotic system as recited in claim 21, wherein the integrated actuator assembly further comprises:
connector means adapted to receive data signals indicating a requested operating state of said bellows means, and to receive power signals; and
receiver means, coupled to said connector means, for distributing said power signals as required by electrical requirements of said actuator assembly, and forwarding said data signals to said microprocessor.

23. The robotic system as recited in claim 22, wherein said microprocessor is responsive to said data signals for generating a command signal that effects the appropriate operation of said valve means consistent with the requested operating state of said bellows means.

24. The robotic system as recited in claim 23, wherein the integrated actuator assembly further comprises memory means, coupled to said microprocessor and including a plurality of position commands each indexed to an operating state of said bellows means, for providing as said command signal the position command corresponding to said requested operating state.

25. The robotic system as recited in claim 21, further comprising:
detection means, in motion-detecting relationship with said bellows means, for detecting a position of said bellows means; and
feedback means, responsive to the detected position of said bellows means and a position command signal from said microprocessor that is representative of a selected motion of said bellows means, for adjusting the operation of said valve means until the position of said bellows means converges to said selected motion.

26. A robotic system comprising:
a plurality of micromanipulative actuator assemblies, each comprising:
a bellow means, responsive to a pressure conditions at an input port and drain port thereof, for generating a motion stimulus;
a valve means, coupled to said bellows means, for operatively regulating the application of a pressure to at least one of the input and drain ports of said bellows means;
a controller means for controlling the operation of said valve means;
a common feed line connecting the input ports of all of said bellows means; and
a common feed line connecting the drain ports of all of said bellows means.

27. In an endoscopic system including a robotic system for maneuvering an implement, said robotic system comprising:
a plurality of micromanipulative actuator assemblies, each comprising:
bellows means, responsive to a pressure conditions at an input port and drain port thereof, for generating a motion stimulus;
valve means, coupled to said bellows means, for operatively regulating the application of a pressure to at least one of the input and drain ports of said bellows means;
controller means for controlling the operation of said valve means;
a common feed line connecting the input ports of all of said bellows means; and
a common feed line connecting the drain ports of all of said bellows means.

28. The apparatus as recited in claim 1, wherein the base comprises silicon.

29. The robotic system as recited in claim 15, wherein the base comprises silicon.

30. The robotic system as recited in claim 15, wherein the robotic movable member is a phalanx of a robotic finger.

31. The robotic system as recited in claim 30, wherein the integrated actuator assembly is located within the robotic finger.

32. A robotic finger comprising:
at least one joint at which two pivotable finger members are pivotably connected; and
an integrated actuator assembly within the robotic finger coupled to one of the pivotable finger members to pivot the pivotable finger members relative to each other, said integrated actuator assembly comprising:
a base;
bellows means, at least partially integrally coupled to said base and responsive to a pressure condition at an input port of said bellows means, for generating a motion stimulus;
valve means, at least partially formed within said base and integrally coupled to said bellows means, for operatively regulating the application of pressure to the input port of said bellows means; and
electronic controller means, at least partially formed within said base, for controlling the operation of said valve means.

33. An integrated apparatus for generating a motion stimulus, said apparatus comprising:
bellows means, responsive to a pressure condition at an input port thereof, for generating a motion stimulus;
pressure generation means for generating pressure at said input port, said pressure generation means comprising source means for generating a flow of pressurized fluid and vacuum means for generating a vacuum pressure;
valve means, integrally coupled to said bellows means, for operatively regulating the application of said pressure at the input port of said bellows means, said valve means comprising:
a first selectively operable micromachined valve adapted to admit the flow of pressurized fluid from said source means into said bellows means, and
a second selectively operable micromachined valve coupled to said vacuum means and adapted to withdraw pressure from said bellows means; and
integral controller means for controlling the operation of said valve means.

34. An integrated apparatus for generating a motion stimulus, said apparatus comprising:
bellows means, responsive to a pressure condition at an input port thereof, for generating a motion stimulus;
pressure generation means for generating pressure at said input port, said pressure generation means comprising source means for generating a flow of pressurized fluid and vacuum means for generating a vacuum pressure;
valve means, integrally coupled to said bellows means, for operatively regulating the application of said pressure at the input port of said bellows means, said valve means comprising a micromachined valve adapted to be selectively coupled to said source means for admitting the flow of pressurized fluid from said source means into said bellows means, or coupled to said vacuum means for withdrawing pressurized fluid from said bellows means; and
integral controller means for controlling the operation of said valve means.

35. In a robotic system including a configuration of robotic fingers, an integrated actuator assembly coupled to said robotic fingers for displacing said robotic fingers, said assembly comprising:
bellows means for generating a motion stimulus as pressurized fluid flows through an input port thereof;
valve means, in fluid communication with the input port of said bellows means, for controllably regulating the fluid flow through the input port of said bellows means, said valve means comprising a configuration of programmable micromachined valves; and
controller means, coupled to said valve means, for controlling the operation of said valve means.

36. In a robotic system including a configuration of robotic fingers, an integrated actuator assembly coupled to said robotic fingers for displacing said robotic fingers, said assembly comprising:
bellows means for generating a motion stimulus as pressurized fluid flows through an input port thereof;
valve means, in fluid communication with the input port of said bellows means, for controllably regulating the fluid flow through the input port of said bellows means;
controller means, coupled to said valve means, for controlling the operation of said valve means, said controller means comprising a microprocessor;
connector means adapted to receive data signals indicating a requested operating state of said bellows means and to receive power signals;
receiver means, coupled to said connector means, for distributing said power signals as required by electrical requirements of said actuator assembly, and forwarding said data signals to said microprocessor, said microprocessor being responsive to said data signals for generating a command signal that effects the appropriate operation of said valve means consistent with the requested operating state of said bellows means; and
memory means, coupled to said microprocessor and including a plurality of position commands each indexed to an operating state of said bellows means, for providing as said command signal the position command corresponding to said requested operating state.

* * * * *

UNITED STATES PATENT AND TRADEMARK OFFICE
CERTIFICATE OF CORRECTION

PATENT NO.: 5,697,285

DATED: December 16, 1997

INVENTOR(S): Bruce Nappi et al.

It is certified that errors in the above-identified patent and that said Letters Patent is hereby corrected as shown below:

Claim 1, column 14, line 50, delete "a" and substitute therefor -- electronic --;

Claim 26, column 16, line 55, delete "a bellow" and substitute therefor -- bellows --;
                line 58, delete "a"; and
                line 62, delete "a".

Signed and Sealed this

Thirty-first Day of March, 1998

Attest:

BRUCE LEHMAN

Attesting Officer          *Commissioner of Patents and Trademarks*